US011382859B1

(12) United States Patent
Brahm

(10) Patent No.: US 11,382,859 B1
(45) Date of Patent: *Jul. 12, 2022

(54) COSMETIC COMPOSITION AND METHODS OF TREATMENT

(71) Applicant: BRAHM HOLDINGS, LLC, Germantown, TN (US)

(72) Inventor: Timothy R. Brahm, Germantown, TN (US)

(73) Assignee: Brahm Holdings, LLC, Germantown, TN (US)

(*) Notice: Subject to any disclaimer, the term of this patent is extended or adjusted under 35 U.S.C. 154(b) by 105 days.

This patent is subject to a terminal disclaimer.

(21) Appl. No.: 16/787,186

(22) Filed: Feb. 11, 2020

Related U.S. Application Data

(63) Continuation of application No. 14/945,547, filed on Nov. 19, 2015, now Pat. No. 10,555,897, which is a continuation of application No. 14/207,756, filed on Mar. 13, 2014, now abandoned.

(60) Provisional application No. 61/802,402, filed on Mar. 16, 2013.

(51) Int. Cl.
| | | |
|---|---|---|
| *A61K 8/98* | (2006.01) | |
| *A61K 35/51* | (2015.01) | |
| *A61K 35/50* | (2015.01) | |
| *A61Q 19/08* | (2006.01) | |
| *A61Q 19/00* | (2006.01) | |
| *A61K 35/48* | (2015.01) | |

(52) U.S. Cl.
CPC .............. *A61K 8/982* (2013.01); *A61K 35/48* (2013.01); *A61K 35/50* (2013.01); *A61K 35/51* (2013.01); *A61Q 19/00* (2013.01); *A61Q 19/007* (2013.01); *A61Q 19/08* (2013.01)

(58) Field of Classification Search
CPC ........ A61K 8/982; A61K 35/48; A61K 35/50; A61K 35/51; A61K 35/007; A61K 35/08; A61Q 19/00
See application file for complete search history.

(56) References Cited

U.S. PATENT DOCUMENTS

| | | | |
|---|---|---|---|
| 3,409,016 A | 11/1968 | Foley | |
| 3,689,668 A | 9/1972 | Piette | |
| 5,036,056 A | 7/1991 | Kludas | |
| 5,612,028 A | 3/1997 | Sackier | |
| 6,152,142 A | 11/2000 | Tseng | |
| 6,326,019 B1 | 12/2001 | Tseng | |
| 7,727,550 B2 | 6/2010 | Siegal | |
| 7,871,646 B2 | 1/2011 | Ghinelli | |
| 8,071,135 B2 | 12/2011 | Cynthia | |
| 8,153,162 B2 | 4/2012 | He | |
| 8,182,840 B2 | 5/2012 | He | |
| 8,182,841 B2 | 5/2012 | He | |
| 8,187,639 B2 | 5/2012 | He | |
| 8,586,540 B2 | 11/2013 | Lee | |
| 8,956,862 B2 | 2/2015 | Totey | |
| 9,694,109 B1* | 7/2017 | Brahm | .......... A61K 35/50 |
| 9,808,491 B2* | 11/2017 | Tseng | .......... A61K 35/50 |
| 2003/0235580 A1 | 12/2003 | Zhang | |
| 2004/0057938 A1 | 3/2004 | Ghinelli | |
| 2007/0020225 A1 | 1/2007 | Matcham | |
| 2007/0021762 A1 | 1/2007 | Liu | |
| 2007/0031471 A1 | 2/2007 | Peyman | |
| 2007/0166819 A1 | 7/2007 | Ghosh | |
| 2007/0292401 A1 | 12/2007 | Brown | |
| 2008/0039940 A1 | 2/2008 | Hashimoto | |
| 2008/0108045 A1 | 5/2008 | Ghinelli | |
| 2008/0181935 A1 | 7/2008 | Ye | |
| 2012/0141595 A1 | 6/2012 | Tseng | |
| 2012/0225484 A1 | 9/2012 | Lugo | |
| 2013/0287741 A1 | 10/2013 | Stilwell | |
| 2013/0344162 A1* | 12/2013 | Morse | ............ A61L 27/3683 424/582 |
| 2014/0037598 A1 | 2/2014 | Yoo | |
| 2014/0050788 A1 | 2/2014 | Sith | |
| 2014/0052247 A1 | 2/2014 | Morse | |

FOREIGN PATENT DOCUMENTS

| | | |
|---|---|---|
| EP | 0285370 A2 | 10/1988 |
| KR | 201000030031 | 3/2010 |
| WO | 8900043 A1 | 1/1989 |
| WO | 8907425 A2 | 8/1989 |
| WO | 2006094247 A2 | 9/2006 |
| WO | 2009052132 A1 | 4/2009 |
| WO | 2011101760 A1 | 8/2011 |
| WO | 2012003377 A2 | 1/2012 |
| WO | 2012047733 A2 | 4/2012 |
| WO | 2013157891 A1 | 10/2013 |

OTHER PUBLICATIONS

Baxter Healthcare Corporation "Plasma-Lyte A", Drugs.com, Aug. 2019 revision (updated as of Jul. 22, 2021), 9 pages. (Year: 2021).*
Avanzi, et al., "Susceptibility of Human Placenta Derived Mesenchymal Stromal/Stem Cells to Human Herpesviruses Infection", PLOS One, vol. 8, Issue 8, pp. 1-14 (Aug. 2013).
Brooke, et al., "Manufacturing of Human Placenta-Derived Mesenchymal Stem Cells for Clinical Trials", British Journal of Haematology, (2008), vol. 144, pp. 571-579.
Fuller, et al., "Stem Cells", Clinical Applications of Cryobiology, (2000), pp. 127-134.
Haimov-Kochman et al. "Modification of the standard trizol-based technique improves the integrity of RNA isolated from RNaserich placental tissue", Clinical Chemistry (2006) 52(1):159-160.
Kagan, "The Skin Bank", Chapter 15, in Total Burn Care, (2012), pp. 199-208.

(Continued)

*Primary Examiner* — Aaron J Kosar
(74) *Attorney, Agent, or Firm* — Barnes & Thornburg LLP

(57) ABSTRACT

A cosmetic composition for the repair and remodeling of the human skin is provided. The cosmetic composition includes a therapeutically effective amount of human birth tissue material and a suitable carrier composition. Methods of treating human skin with the cosmetic composition, methods of reducing the appearance of a skin condition arising from aging and a corresponding kit are also provided.

15 Claims, No Drawings

(56) References Cited

OTHER PUBLICATIONS

Parolini et al., "Concise Review: Isolation and Characterization of Cells from Human Term Placenta: Outcome of the First International Workshop on Placenta Derived Stem Cells", Stem Cells (2008), vol. 26, pp. 300-311.

Sabapathy, et al., "Long-Term Cultured Human Term Placenta-Derived Mesenchymal Stem Cells of Maternal Original Displays Plasticity", Stem Cells International, (2012), vol. 2012, pp. 1-11.

* cited by examiner

COSMETIC COMPOSITION AND METHODS OF TREATMENT

CROSS-REFERENCE TO RELATED APPLICATIONS

This application is a continuation of U.S. application Ser. No. 14/945,547, filed Nov. 19, 2015, now U.S. Pat. No. 10,555,897, which is a continuation of U.S. application Ser. No. 14/207,756 filed Mar. 13, 2014 which claims priority to U.S. Provisional Patent Application No. 61/802,402 filed Mar. 16, 2013, the contents of which are each incorporated herein in their entirety.

FIELD OF THE INVENTION

A cosmetic composition for the repair and remodeling of the human skin is provided. Methods of treating human skin with the cosmetic composition, methods of reducing the appearance of a skin condition arising from aging and a corresponding kit are also provided.

BACKGROUND OF THE INVENTION

As the largest organ of the human body, the skin plays a vital role in protecting the body's internal organs from external forces in the environment. The skin is regularly insulted by radiation from the sun, wind, dust, dirt and harmful chemicals. The skin is also subject to routine maintenance which includes washing, shaving, and the application of various chemicals found in cosmetic formulations. Such insults and routines contribute to the aging of skin which manifests in the appearance of lines, wrinkles, skin fading, age spots, elasticity failure, and skin dryness. The skin is also susceptible to other conditions resulting from an underlying disease or condition which, if left untreated, can lead to serious discomfort or illness.

Various attempts have been made to prepare cosmetic formulations (creams, oils, gels, etc.) that prevent or reverse the normal skin aging process in an attempt to maintain a youthful appearance. Such formulations, however, often contain harsh or toxic ingredients that lead to side effects such as pain, redness, or inflammation. Thus, there remains a need in the art for a cosmetic composition that provides anti-aging properties and treats various skin conditions and disorders in an easy to use, safe, and cost-effective formulation.

SUMMARY OF THE INVENTION

According to one aspect, a cosmetic composition is provided. The cosmetic composition includes a therapeutically effective amount of human birth tissue material and a suitable carrier composition. According to one embodiment, the birth tissue material includes one or more components of a human placental organ such as the placental globe, umbilical cord, umbilical cord blood, chorionic membrane, amniotic membrane, Wharton's jelly or amniotic fluid. According to one embodiment, the carrier composition is present in an amount from about 0.1% to about 99.0%. According to one embodiment, the birth tissue material is present in an amount from about 0.1% to about 99.0%. According to one embodiment, the carrier composition is formulated as a cream, emulsion, lotion, gel, ointment, salve, butter, gel, putty, or balm.

According to another aspect, a method of treating a skin condition or soft tissue defect of the skin is provided. According to one embodiment, the method includes the step of applying to the skin condition or soft tissue defect of the skin an effective amount of the cosmetic composition as described herein. According to one embodiment, the skin condition is an ischemic wound, scar, traumatic wound, severe burn, or surgical wound. According to one embodiment, the skin condition is keratosis, melasma, pruritus, spider veins, lentigo, dermatitis, psoriasis, folliculitis, rosacea, ance, impetigo, erysipelas, erythrasma, or eczema.

According to another aspect, a method of reducing the appearance of a skin condition arising from aging is provided. According to one embodiment, the method includes the step of applying an effective amount of the composition as described herein to the skin condition. The application of the composition reduces the appearance of the skin condition. According to one embodiment, the skin condition is rhytids, elastosis, purpura, angiomas, general dryness, general itchiness, skin tags, warts, or dyschromia. According to one embodiment, the skin condition is located on facial skin.

According to yet another aspect, a kit comprising the cosmetic composition as described herein is provided. According to one embodiment, the kit includes instructions for use thereof.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human birth tissue" encompasses one or more of the components of the placental organ including, but not limited to, the placental globe, the umbilical cord, the umbilical cord blood, the chorionic membrane, the amniotic membrane, the Wharton's jelly, other gelatins, cells, and extracellular material, and the amniotic fluid.

As used herein, "placental tissue components" encompasses one or more of the tissue components of the placental organ including, but not limited to, the placental globe, the umbilical cord, the umbilical cord blood, the chorionic membrane, the amniotic membrane, the Wharton's jelly and other gelatins, cells and extracellular material.

As used herein, the term "amnion" and "amniotic membrane" are used interchangeably.

A cosmetic composition is provided. The cosmetic composition includes human birth tissue and an acceptable carrier composition. The human birth tissue can be prepared according to the steps provided herein and combined with the carrier composition to formulate a cosmetic composition suitable for routine application to any part of the human skin to cease or reverse various signs of aging or treat a particular skin condition or disorder. The cosmetic composition can be storage stable and color stable.

To prepare the human birth tissue material for inclusion in a cosmetic composition, placental tissue components and amniotic fluid are initially recovered from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

According to one embodiment, the placental tissue components include one or more components selected from the group consisting of amniotic membrane, chorionic membrane, Wharton's jelly, umbilical cord tissue, umbilical cord blood, placental globe, and other gelatins, other cells and extracellular matrix from placental tissue components. Other variations of the invention include, however, removing one or more of the placental globe, umbilical cord tissue, umbilical cord blood, chorionic membrane, amniotic membrane, or Wharton's jelly before further processing. Removal of one or more of the placental tissue components can be achieved via a sterile saline solution rinse, blunt dissection, scalpel, or a combination thereof, if necessary.

The retained placental tissue components can be placed in a sterile transport solution after aseptic recovery. The sterile transport solution is used to provide an advantageous medium to the natural function of tissue components prior to processing. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 10% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

Optionally, the placental tissue components may be soaked in a sterile saline solution for one or more soaks to remove all maternal components. In one embodiment, the sterile saline solution includes NaCl in a concentration range from typically about 10% to typically about 15% by weight.

Optionally, the placental tissue components can be cryopreserved according to methods commonly used in the art. The placental tissue components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

The birth tissue material can be subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, hand pressing, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. After morselization, the milled human birth tissue material can be retained and preserved until combined with the carrier composition as described herein to formulate the final cosmetic composition.

In one embodiment, the tissue may be morselized or otherwise rendered into fine particulates. Particles may be micron or submicron size ranges. In one embodiment, particle sizes may range from 1 micron to 100 microns. In another embodiment, particle sizes may range from 10 nm to 100 nm. Particles must be of sufficient size to allow diffusion through skin.

The carrier composition can include any variety of components suitable for application to the human skin. According to one embodiment, the carrier composition includes one or more vitamins, minerals, proteins, fats, collagens (including collagen extracted from the placental globe), waxes, glycols and derivatives thereof, glyercols and derivatives thereof, oils (including essential oils), skin-abrading granules, fatty acids, cholesterols, alcohols, emollients, adsorbents, lubricants, moisturizing agents, emulsifying agents, thickening agents, humectants, surfactants, pharmaceutical ingredients, preservatives, antifungal agents, antioxidants, antimicrobial agents, structuring agents, dispersing agents, UV blocker and absorber ingredients (sunscreen), pH-adjusting components, sequestering or chelating agents, wetting agents and other components known in the art to be suitable for use in a cosmetic composition.

The carrier composition can include other suitable components including, but not limited to, water, retinol, sorbitol, lanolin, beeswax, oleic acid, spermaceti, almond oil, egg oil, aloe, castor oil, tracacanth gum, clay, magnesia, talc, metal stearates, chalk, magnesium carbonate, zinc stearate, kaolin, glycerin, propylene glycol, polyethylene glycol, hyaluronic acid, chondroitin sulfate, elastin, polysaccharide, glycosaminoglycan, ascorbic acid, ascorbic acid derivatives, glucosamine ascorbate, arginine ascorbate, lysine or tyrosine ascorbate, gluthathione ascorbate, nicotinamide ascorbate, niacin ascorbate, allantoin ascorbate, creatine ascorbate, creatinine ascorbate, chondroitin ascorbate, chitosan ascorbate, DNA ascorbate, alpha hydroxyl acids, carnosine ascorbate, tocotrienol, rutin, quercetin, hesperedin, diosmin, mangiferin, mangostin, cyanidin, astaxanthin, lutein, lycopene, resveratrol, tetrahydrocurcumin, rosmarinic acid, hypericin, ellagic acid, chlorogenic acid, oleuropein, alpha-lipoic acid, niacinamide lipoate, gluthathione, andrographolide, carnosine, niacinamide, polyphenols, pycnogenol and mixtures thereof, benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof; antiacne agents such as salicylic acid; skin bronzing or tanning agent ingredients such as dihydroxyacetone, erytrulose, melanin; antioxidants such as vitamin C and derivatives thereof (e.g. ascorbyl acetate, ascorbyl phosphate and ascorbyl palmitate), vitamin A and derivatives thereof; folic acid and derivatives thereof; vitamin E and derivatives thereof such as tocopheryl acetate, flavons, or flavonoids, amino acids such as histidine, glycine, tyrosine, tryptophan, and derivatives thereof; carotenoids and carotenes; uric acid and derivatives thereof; citric acid, lactic acid, malic acid; stilbenes and derivatives thereof; and pomegranate extracts; vitamin K1 or K2, vitamin K1 oxide or vitamin K2 oxide, hormones, plant or botanical extracts, anti-inflammatory agents, concentrates of plant extracts, silicones, skin soothing ingredients, analgesics or anti-itch agents, skin penetration enhancers, solubilizers, alkaloids and processing aids; coloring agents including various dyes and pigments; perfumes or fragrances for the body; and other suitable components that do not interfere with the interaction between the birth tissue material and the various layers of the human skin.

The carrier composition is formulated in such a way that the combination of the birth tissue material and carrier composition are chemically compatible and do not form complexes which precipitate from the final cosmetic composition. According to one embodiment, the carrier composition can be formulated as a cream, emulsion, lotion, gel, ointment, salve, butter, gel, putty, or balm. According to a preferred embodiment, the carrier composition is a cream.

Various techniques known in the art may be utilized for preparing the cosmetic composition. According to one embodiment, the human birth tissue and the carrier composition as provided herein are mixed or blended according to a variety of conventional techniques. According to one embodiment, the human birth tissue and the carrier composition mixed in a manner to produce a smooth and homogenous composition. According to one embodiment, the human birth tissue as provided herein is introduced to the carrier composition after the carrier composition is formed (i.e., post-added). In an alternative embodiment, the human birth tissue is introduced during carrier composition preparation. The amount of human birth tissue material present in the cosmetic composition can vary depending upon the chosen carrier composition, the frequency of use, and the severity of the skin defect or condition to be treated. According to one embodiment, the cosmetic composition includes from typically about 0.1% to about 99.0% birth tissue material based on total cosmetic composition weight. Optionally, a suitable amount of amniotic fluid components may also be combined with the carrier composition. Bioactive agents such as physiologically compatible minerals, growth factors, antibiotics, chemotherapeutic agents, antigen, antibodies, enzymes, vectors for gene delivery and hormones may also be added to the carrier composition. The amount of carrier composition present in the final cosmetic composition can vary according to the final formulation of the cosmetic composition. According to one embodiment, the carrier composition components can be present in an amount from typically about 0.1% to about 99.0% based on total cosmetic composition weight.

Methods of treating various signs of skin aging are provided. According to one embodiment, the cosmetic composition as provided can be used for ceasing or reversing various signs of aging which include, but are not limited to, rhytids (e.g., crow's feet, marionette marks, neck bands, frown lines), elastosis (e.g., face and neck), pigmented spots, purpura, angiomas, general dryness, general itchiness, skin tags, warts, and dyschromia (hyperpigmentation or hypopigmentation).

Methods of treating a soft tissue defect or skin condition are also provided. For example, the cosmetic composition as provided herein can be used for sealing, molding, filling and/or otherwise treating a soft tissue defect on the skin of a patient. The skin condition can be caused by exposure to UV light, age, irradiation, chronic sun exposure, environmental pollutants, air pollution, wind, cold, heat, chemicals, disease pathologies, smoking, or lack of nutrition. Soft tissue defects that can be treated by the present cosmetic composition further include skin conditions such as, for example, ischemic wounds, scar revision or the treatment of traumatic wounds, severe burns, surgical wounds as well as treatment of cosmetic conditions (e.g., those involving repair or augmentation). Other skin conditions include, but are not limited to, keratosis, melasma, pruritus, spider veins, lentigo, dermatitis, psoriasis, folliculitis, rosacea, acne, impetigo, erysipelas, erythrasma, and eczema.

In use, the area of skin subject to application is initially washed and dried. A generous amount can then be placed on the fingertips or an appropriate delivery device such as a cloth or sponge. The composition can be dispensed in a spray, dollop, or liquid, aerosol, a fluid, or a semi-solid. The cosmetic composition may also be delivered in various consumer vehicles such as, for example, a lipstick, cleanser, toner, sunscreen, mask, bandage, foundation, or lotion. The cosmetic composition can then be applied onto the skin at the area to be treated. Optionally, the cosmetic composition can be rubbed into the skin using the fingertips. The cosmetic composition can be applied once or multiple times daily or as needed to repair a skin defect or condition or cease or reverse any signs of aging. The cosmetic composition can be applied to any part of the human skin in need including, but not limited to the facial skin, arm skin, leg skin, chest skin, abdomen skin, and back skin.

Also provided herein is a kit that includes a cosmetic composition as described herein. Such kits can include a package that is adapted to receive one or more containers, each of the container(s) including a cosmetic composition as described herein. Containers can include a bottle, a vial, a metal tube, a laminate tube, a plastic tube, a dispenser, a pressurized container, a barrier container, a compartment, a lipstick container, a compact container, cosmetic pans that can hold cosmetic compositions, or other types of containers such as glass or injection or blow-molded plastic containers. The containers can dispense a pre-determined amount of the composition. In other embodiments, the container can be squeezed (e.g., metal, laminate, or plastic tube) to dispense a desired amount of the composition. The containers can have spray, pump, or squeeze mechanisms. The kit is appropriately preserved up until and during shipment to a distributor or medical facility. The kit additionally includes at least one set of instructions for the end user including an explanation of how to apply, use, and maintain the cosmetic composition.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Prophetic Example 1

A cosmetic composition formulated for hydration and aging repair can be prepared as provided herein. The resulting composition can appear as a white, mobile, full-bodied cream. Preferably, the cosmetic composition glides on the skin smoothly, without tackiness and absorbs within minutes.

The particular components and amounts of a prophetic carrier composition are provided in Table 1.

TABLE 1

| Component | Amount (% weight) |
|---|---|
| PHASE A | |
| Distilled or Purified Water | 61.7% |
| Hyaluronic Acid | 5.0% |
| Dimethylaminoethanol | 0.8% |
| Gluconolactone (preservative) | 2.0% |
| PHASE B | |
| Glyceryl Stearate/Cetearyl Alcohol/ Sodium Stearoyl Lactylate mixture | 7.0% |
| Jojoba Oil | 6.0% |
| Macadamia Nut Oil | 1.0% |
| PHASE C | |
| Vitamins A, B3, B5, C and E | 12.0% |
| Palmitoyl Tripeptide-5 | 3.0% |
| Silk Protein (hydrolyzed) | 1.0% |
| Essential Oils (e.g., lavendar, peppermint, grapefruit, etc.) | 0.5% |

To prepare the carrier composition, the components of Phase A are initially combined and mixed well. The Phase A mixture is then heated to 170° F. Next, the components of Phase B are added to the Phase A mixture, mixed, and heated to 170° F. The Phase A and Phase B combination is then allowed to cool to 110° F. After cooling to at or below 170° F., the Phase C components are mixed in to the Phase A/Phase B combination and allowed to cool thereby rendering a carrier composition. Lastly, a particular birth tissue material may be mixed with the resulting carrier composition to form one embodiment of the cosmetic composition of the present disclosure.

I claim:

1. A cosmetic composition for treating a skin condition comprising:
    a therapeutically effective amount of at least one human birth tissue material including one or more components of a human placental organ selected from the group consisting of placental globe, umbilical cord, umbilical cord blood, chorionic membrane, amniotic membrane, Wharton's jelly, extracellular material, and amniotic fluid;
    a nanoparticle composition; and
    a suitable carrier composition,
    wherein the cosmetic composition treats the skin subject to the skin condition.

2. The cosmetic composition of claim 1, wherein the birth tissue material includes one or more components of a human placental organ selected from the group consisting of morselized placental globe, morselized umbilical cord, morselized chorionic membrane, morselized amniotic membrane, and amniotic fluid.

3. The cosmetic composition of claim 1, wherein the carrier composition is present in an amount from about 0.1% to about 99.0%.

4. The cosmetic composition of claim 1, wherein the birth tissue material is present in an amount from about 0.1% to about 99.0%.

5. The cosmetic composition of claim 1, wherein the carrier composition is formulated as a cream, emulsion, lotion, gel, ointment, salve, butter, gel, putty, or balm.

6. The cosmetic composition of claim 1, wherein the skin condition is selected from the group consisting of an ischemic wound, scar, traumatic wound, severe burn, and surgical wound.

7. The cosmetic composition of claim 1, wherein the skin condition is selected from the group consisting of keratosis, melasma, pruritus, spider veins, lentigo, dermatitis, psoriasis, folliculitis, rosacea, impetigo, erysipelas, erythrasma, and eczema.

8. The cosmetic composition of claim 1, wherein the carrier composition includes amniotic fluid.

9. The cosmetic composition of claim 1, wherein the nanoparticle composition includes one or more elemental ion nanoparticles selected from the group consisting of silver, gold, magnesium, copper, aluminum, titanium, indium, cobalt, nickel, silicon, zirconium, samarium, lanthanum, and zinc.

10. The cosmetic composition of claim 1, wherein the nanoparticle composition includes one or more elemental nanoparticles selected from the group consisting of silver, gold, magnesium, copper, aluminum, titanium, indium, cobalt, nickel, silicon, zirconium, samarium, lanthanum, and zinc.

11. The cosmetic composition of claim 1, wherein the nanoparticle composition includes one or more impurities selected from the group consisting of osmium, rhenium, rhodium, tin, platinum, lithium, sodium, silver, zinc, silicon, carbon, nitrogen, sulfur, iron, molybdenum, rubidium, copper, and potassium.

12. The cosmetic composition of claim 1, wherein the placental construct exhibits antimicrobial, antiviral, antifungal, angiogenic, neurogenic, collagenic, osteogenic properties, or any combination thereof.

13. The cosmetic composition of claim 1, wherein the carrier composition includes one or more vitamins, minerals, proteins, fats, collagens, waxes, glycols, glycerols, oils, skin-abrading granules, fatty acids, cholesterols, alcohols, emollients, adsorbents, lubricants, moisturizing agents, emulsifying agents, thickening agents, humectants, surfactants, preservatives, antifungal agents, antioxidants, antimicrobial agents, structuring agents, dispersing agents, UV blockers, pH-adjusting components, sequestering or chelating agents, and wetting agents.

14. A kit comprising the cosmetic composition of claim 1.

15. The kit of claim 14, further comprising instructions for use thereof.

\* \* \* \* \*